(12) United States Patent
Funakubo et al.

(10) Patent No.: US 7,280,208 B2
(45) Date of Patent: Oct. 9, 2007

(54) OPTICAL CHARACTERISTIC ANALYSIS METHOD, SAMPLE MEASURING APPARATUS AND SPECTROSCOPIC ELLIPSOMETER

(75) Inventors: Hiroshi Funakubo, Yokohama (JP); Yoshihisa Honda, Matsudo (JP); Nataliya Nabatova-Gabain, Kyoto (JP); Asuka Terai, Kyoto (JP)

(73) Assignee: Horiba, Ltd., Minami-Ku, Kyoto (JP)

( * ) Notice: Subject to any disclaimer, the term of this patent is extended or adjusted under 35 U.S.C. 154(b) by 45 days.

(21) Appl. No.: 11/196,808

(22) Filed: Aug. 2, 2005

(65) Prior Publication Data
US 2006/0023213 A1 Feb. 2, 2006

(30) Foreign Application Priority Data
Aug. 2, 2004 (JP) .............................. 2004-225991

(51) Int. Cl.
*G01J 4/00* (2006.01)
(52) U.S. Cl. ..................................... 356/364
(58) Field of Classification Search ..................... None
See application file for complete search history.

(56) References Cited

U.S. PATENT DOCUMENTS 6,008,906 A * 12/1999 Maris ......................... 356/432
6,413,659 B1 7/2002 Rothberg 2002/0021137 A1* 2/2002 Takeuchi .................... 324/753

FOREIGN PATENT DOCUMENTS

JP   63-205543 A   8/1988
JP   64-41838 A    2/1989

OTHER PUBLICATIONS

Wang et al., "Electro-optic measurements of thin-film materials by means of Reflection Differential Ellipsometry", J. Appl. Phys. 78(1), (Jul. 1995), pp. 9-15.
Wang et al., "Electro-optic properties of oxide ferroelectrics grown on GaN/sapphire", J. Appl. Phys. vol. 88, No. 3 (Aug. 2000), pp. 1701-1703.
Hale and Woollam, "Prospects for IR emissivity control using electrochromic structures", Thin Solid Films vol. 339 (1999), pp. 174-180.

(Continued)

*Primary Examiner*—Tu T. Nguyen
(74) *Attorney, Agent, or Firm*—Darby & Darby

(57) ABSTRACT

The spectroscopic ellipsometer, by a computer program incorporated therein, applies voltage to a sample placed on a stage, with a power supply device and conducting probe stands, polarizes multi-wavelength light, with a light polarizer, generated by a xenon lamp and irradiates the polarized light to the sample. The sample is provided with a multilayer film and electrodes formed on a substrate and the sample's surface, and light reflected from the sample is received by the light receiver and measured by the spectrometer. The computer analyzes the optical characteristic of the sample individually for each layer of the multilayer film on the basis of the measurement result and a value calculated from a model which is formed according to the sample structure.

17 Claims, 9 Drawing Sheets

OTHER PUBLICATIONS

Trimble et al., "Infrared emittance modulation devices using electrochromic crystalline tungsten oxide, polymer conductor, and nickel oxide", Thin Solid Films vol. 355-356 (1999), pp. 26-34.

Jellison et al., "Electric-field- induced birefringence in $LiNbO_3$ measured by generalized Transmission ellipsometry", Appl. Phys. Lett. vol. 81, No. 7 (Aug. 2002), pp. 1222-1224.

Jellison et al., "Internal electric field measurements in cadmium zinc telluride using transmission two-modulator generalized ellipsometry", J. of electronic materials vol. 32, No. 7 (Jul. 2003), pp. 789-795.

E. B. Franke et al., "Infrared switching electrochromic devices based on tungsten oxide", J. Appl. Phys. vol. 88, No. 10 (Nov. 2000), pp. 5777-5784.

Buckman and Bashara, "Electroreflectance changes in dielectric constants of Au and Ag by modulated ellipsometry", Phys. Rev. vol. 174, No. 3 (Oct. 1968), pp. 719-721.

Fukazawa et al., "Application of time-resolved spectroellipsometry to the study of liquid crystal reorientation on dynamics", Thin Solid Films vol. 313-314 (1998), pp. 799-802.

\* cited by examiner

OPTICAL CHARACTERISTIC ANALYSIS METHOD, SAMPLE MEASURING APPARATUS AND SPECTROSCOPIC ELLIPSOMETER

CROSS-REFERENCE TO RELATED APPLICATIONS

This Nonprovisional application claims priority under 35 U.S.C. §119(a) on Patent Application No. 2004-225991 filed in Japan on Aug. 2, 2004, the entire contents of which are hereby incorporated by reference.

BACKGROUND OF THE INVENTION

1. Field of the Invention

The present invention relates to an optical characteristic analysis method, a sample measuring apparatus and a spectroscopic ellipsometer, with which the optical characteristic of a multilayer film can be analyzed, with voltage being applied thereto, in order to evaluate the electro-optic effect of the material with a multilayer film structure.

2. Description of Related Art

Conventionally, a substance provided with a high-dielectric constant film or a ferroelectric film, formed on a substrate, is used as the material to produce a ferroelectric memory, a ferroelectric capacitor, a piezoelectric element, such an actuator, and an electro-optic device, such as an optical shutter and an optical isolator, and the like. To specify the characteristic of a film of such material is extremely important for influencing the memory performance or the like, and a refractive index, a transmittance and the like change with electric field being applied thereto, known as the electro-optic effect, so for example, the above mentioned features are used in order to evaluate the characteristic of a film.

FIG. 1 is a schematic view showing a conventional measurement method of electro-optic effect. In this measurement method, a pyramidal prism coupling P is placed on the surface of a sample S provided with a film S2 formed on a substrate S1, light is irradiated to the prism coupling P, with required electric field being applied to the sample S, and a refractive index of light, which is projected to the sample S by the prism coupling P, is measured by a required measuring apparatus.

It should be noted that measurement of the electro-optic effect is disclosed also in Japanese Patent Application Laid-Open No. S63-205543 (1988) and Japanese Patent Application Laid-Open No. H1-41838 (1989).

In the conventional measurement method shown in FIG. 1, since a measurement is made with the prism coupling P being placed on the surface of the sample S, there is a problem that a sample S of large size, having a dimension at least sufficient for placing the prism coupling P, needs to be prepared. Moreover, since it is necessary to polish the surface of the sample S, on which the prism coupling P is placed, until a required smoothness is obtained, in order to prevent occurrence of unwanted refraction at the boundary between the prism coupling P and the sample S, there is a problem that preparation of the sample S needs a lot of effort. Furthermore, since a measurement is made for a location where light is projected by the prism coupling P in the conventional measurement method, there is a problem that it becomes extremely difficult to make a so-called in-plane distribution measurement of refractive index for finding out how the refractive index is distributed on the entire surface of the sample S. Moreover, even when the method according to Japanese Patent Application Laid-Open No. S63-205543 (1988) and Japanese Patent Application Laid-Open No. H1-41838 (1989) is used, the in-plane distribution measurement of refractive index, which requires movement of a location of the sample where light is irradiated, needs a lot of effort and time and a measurement cannot be made easily.

On the other hand, when a sample to be measured is a substance provided with a high-dielectric constant film or a ferroelectric film formed on a substrate, it has been reported that an unknown film is automatically formed on the substrate, with the formation of the high-dielectric constant film or the ferroelectric film, and a multilayer film structure (structure having a plurality of layers) is formed as a result. Considering utilization of this substance as the material of a ferroelectric memory, a ferroelectric capacitor or the like, it is extremely important to measure the characteristic of such a multilayer film individually for each layer. A measurement for each layer, however, cannot be made with the conventional measurement method shown in FIG. 1 and, moreover, to measure accurately is difficult even with the method according to Japanese Patent Application Laid-Open No. S63-205543 (1988) and Japanese Patent Application Laid-Open No. H1-41838 (1989).

BRIEF SUMMARY OF THE INVENTION

The present invention has been made with the aim of solving the above problems, and it is an object of the present invention to provide an optical characteristic analysis method, a sample measuring apparatus and a spectroscopic ellipsometer, with which the optical characteristic of a sample, with electric field being applied thereto, can be analyzed accurately for each layer, using an apparatus such as a spectroscopic ellipsometer capable of analyzing the characteristic of each layer of a sample having a multilayer film structure.

Another object of the present invention is to provide an optical characteristic analysis method and a spectroscopic ellipsometer, with which a sample can be moved, with electric field remaining applied, so that the in-plane distribution of refractive index of a sample can be analyzed easily.

Yet another object of the present invention is to provide an optical characteristic analysis method and a spectroscopic ellipsometer, with which a sample can be analyzed effectively in conjunction with a change in the electric field intensity.

In order to achieve the above objects, an optical characteristic analysis method according to the first aspect is an optical characteristic analysis method for analyzing an optical characteristic of a sample comprising a film of a plurality of layers with a spectroscopic ellipsometer, characterized by a first step of applying voltage to the sample; a second step of irradiating polarized light of a plurality of wavelength components to film surface of the sample to which voltage is applied; and a third step of measuring a polarization state of the light reflected from the sample and analyzing optical characteristic of the film of the sample for each layer.

An optical characteristic analysis method according to the second aspect is an optical characteristic analysis method for analyzing optical characteristic of a sample, which includes a film of a plurality of layers and a plurality of electrodes and has an optically transparent electrode covering the film, among the plurality of electrodes, with a spectroscopic ellipsometer, characterized by a first step of applying voltage across electrodes of the sample; a second step of irradiating polarized light of a plurality of wavelength components to surface of the optically transparent electrode of the sample to which voltage is applied; and a third step of measuring a polarization state of light reflected from the sample and analyzing optical characteristic of the film of the sample for each layer.

An optical characteristic analysis method according to the third aspect is characterized in that a value of voltage to be applied is changed in the first step, and the second step and the third step are performed for each value of changed voltage.

An optical characteristic analysis method according to the fourth aspect is characterized in that a location where light is irradiated is sequentially moved in the second step and optical characteristic is analyzed for each moved location in the third step.

A sample measuring apparatus according to the fifth aspect is a sample measuring apparatus that includes generating means for generating light having a plurality of wavelength components; irradiating means for polarizing light generated by the generating means and irradiating the light to a sample, placed on a sample support; and measuring means for detecting and measuring light reflected from the sample, characterized by further including voltage applying means for applying voltage to the sample, placed on the sample support, wherein the irradiating means is constructed to irradiate light to the sample to which the voltage applying means applies voltage.

A spectroscopic ellipsometer according to the sixth aspect is a spectroscopic ellipsometer for irradiating polarized light to a sample, placed on a sample support, and analyzing characteristic of the sample on the basis of a measurement of a polarization state of light reflected from the sample, characterized by including a voltage applying means for applying voltage to the sample, placed on the sample support, wherein an analysis is made by irradiating light to the sample to which the voltage applying means applies voltage.

A spectroscopic ellipsometer according to the seventh aspect is characterized in that the voltage applying means is a contact means that comes in electrical contact with the sample and power supply means for supplying power to the contact means, and the power supply means is constructed so as to change a voltage value of the power supply.

A spectroscopic ellipsometer according to the eighth aspect is characterized by further including means for analyzing the sample for each voltage value, changed by the power supply means.

A spectroscopic ellipsometer according to the ninth aspect is characterized by further including moving means for moving the sample support, wherein the contact means is provided at the sample support.

A spectroscopic ellipsometer according to the tenth aspect is characterized by further including means for analyzing the sample for each movement made by the moving means.

With the first aspect and the sixth aspect, since a spectroscopic ellipsometer analyzes a sample, with a voltage being applied thereto, the optical characteristic of a film of a plurality of layers provided at the sample can be analyzed for each layer. As a result, it becomes possible to evaluate the electro-optic effect of a sample, having a multilayer film structure, measurement of which is difficult with conventional measurement methods, for each layer and, therefore, an unknown film, which is generated with the formation of a high-dielectric constant film or a ferroelectric film, can also be analyzed separately from other films, thereby attributing research, manufacturing and the like of the material of a ferroelectric memory, a ferroelectric capacitor, a piezoelectric element, an electro-optic device and the like.

With the second aspect, since light is irradiated to the surface of an optically transparent electrode of a sample, which has an optically transparent electrode covering a film of a plurality of layers, the degree of freedom of an angle and a location of light irradiation is enhanced and an effective analysis process can be performed. It should be noted that a transparent electrode which transmits light, an electrode having an extremely small thickness so as to transmit light or the like corresponds to the optically transparent electrode.

With the third aspect and the eighth aspect, since the value of voltage to be applied is changed and an analysis is made for each changed value, the relation between the intensity of generated electric field and the electro-optic effect can be analyzed effectively and, as a result, the optical characteristic according to the electric filed of a sample can be analyzed easily.

With the fourth aspect and the tenth aspect, since a location where light is irradiated is sequentially moved and an analysis is made for each moved location, consecutive analysis of a plurality of locations of a sample, which is difficult with conventional measurement methods, is possible and, as a result, it becomes possible to make an in-plane analysis of the sample easily.

With the fifth aspect, since a sample measuring apparatus for irradiating light, having a plurality of wavelength components, to a sample and measuring is provided with voltage applying means for applying voltage to a sample, it becomes possible to measure a sample with voltage being applied thereto and to evaluate, for example, the electro-optic effect of a sample having a multilayer film structure, measurement of which is difficult with conventional measurement methods, for each layer, thereby attributing to research, manufacturing and the like of a ferroelectric memory, a ferroelectric capacitor, a piezoelectric element, an electro-optic device and the like.

With the seventh aspect, since contact means to come in electrical contact with a sample and power supply means for varying a voltage value of the power supply are provided, it becomes possible to analyze the sample with a variety of voltage values and to analyze the characteristic of the sample in detail.

With the ninth aspect, since the sample support is made movable and contact means to come in electrical contact with a sample is provided at the sample support, the contact means can be moved integrally with the sample support, electrical contact can be maintained, even when the location of the sample where light is irradiated is changed, by the movement of the sample support and, therefore, a favorable analysis environment can be provided.

With the first aspect and the sixth aspect, since a spectroscopic ellipsometer analyzes a sample with voltage being applied thereto, it becomes possible to evaluate the electro-optic effect of the sample having a multilayer film structure, for which measurement is difficult with conventional measurement methods, for each layer.

With the second aspect, since light is irradiated to the surface of an optically transparent electrode of a sample, which has an optically transparent electrode covering a film of a plurality of layers, a form of light irradiation according to the form of the sample can be ensured.

With the third aspect and the eighth aspect, since a value of voltage to be applied is changed and an analysis is made for each changed value, the relation between the intensity of generated electric field and the electro-optic effect can be analyzed effectively.

With the fourth aspect and the tenth aspect, since a location where light is irradiated is sequentially moved and an analysis is made for each moved location, consecutive analysis of a plurality of locations of a sample is made, so that an in-plane analysis of the sample can be performed easily.

With the fifth aspect, since voltage applying means for applying voltage to a sample is provided, it becomes possible to measure a sample with voltage being applied thereto and to attribute evaluation of the electro-optic effect of a sample having a multilayer film structure for each layer.

With the seventh aspect, since contact means to come in electrical contact with a sample and power supply means for varying a voltage value related to power supply are provided, it becomes possible to analyze the sample with a variety of voltage values.

With the ninth aspect, since the sample support is made movable and contact means to provide an electrical contact with a sample is provided at the sample support, the contact means can be moved integrally with the sample support, electrical contact can be maintained by the movement of the sample support, even when the location of the sample where light is irradiated is changed.

The above and further objects and features of the invention will more fully be apparent from the following detailed description with accompanying drawings.

DETAILED DESCRIPTION OF THE INVENTION

Figure 1:
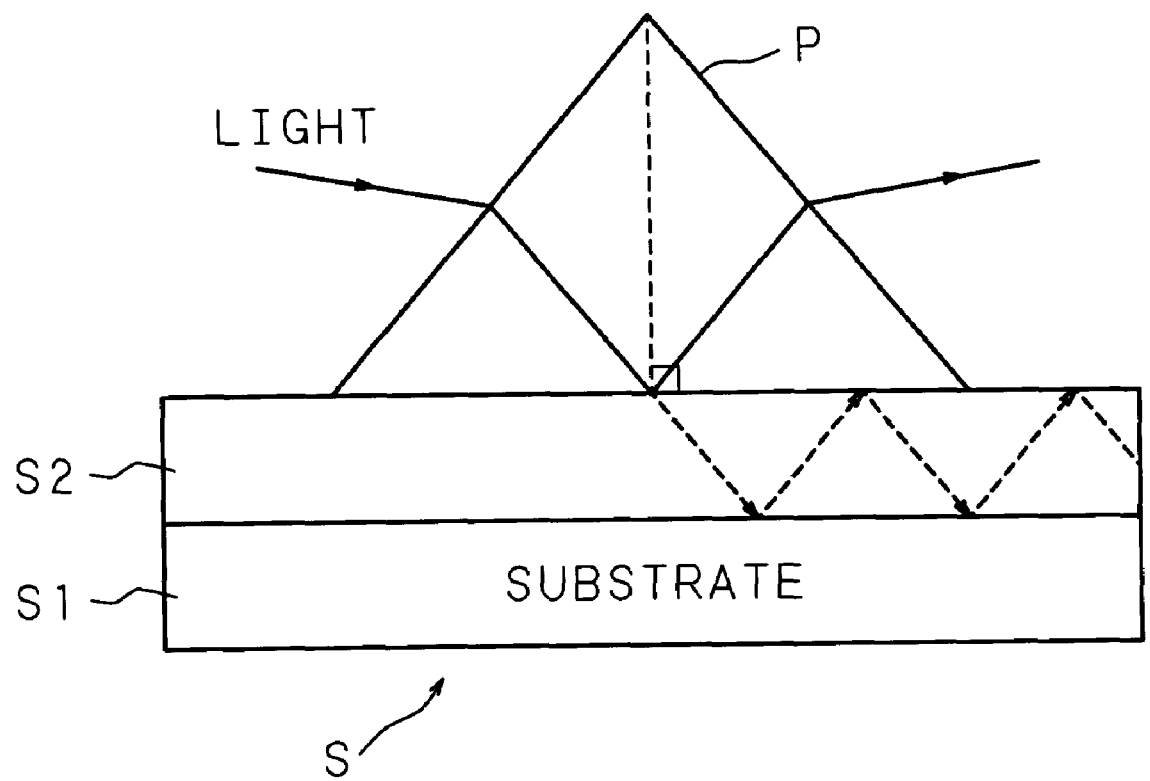
FIG. 1 is a schematic view showing a conventional analysis method.
Figure 2:
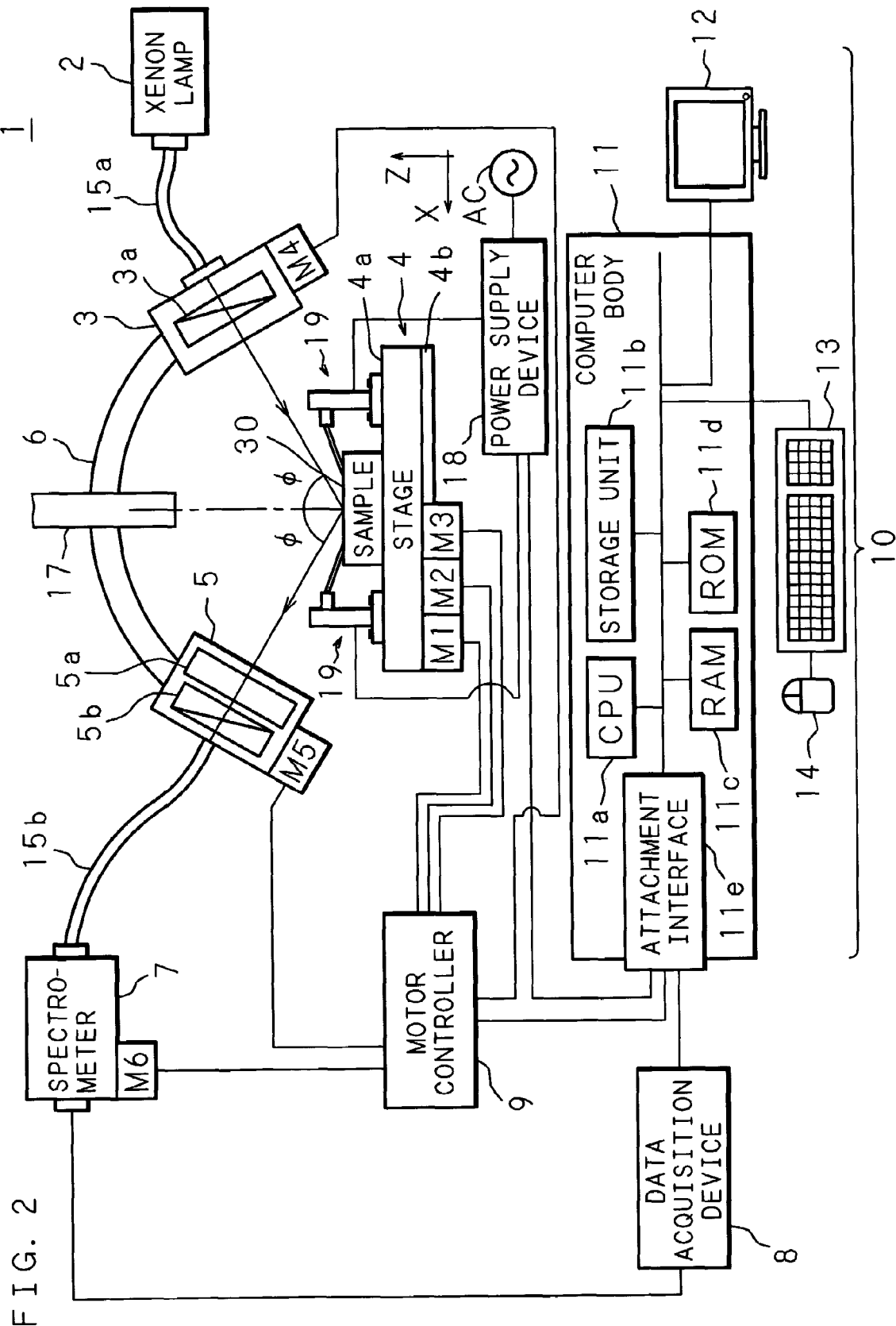
FIG. 2 is a general structure view of a spectroscopic ellipsometer according to an embodiment of the present invention.

FIG. 2 is a schematic view showing the general structure of a spectroscopic ellipsometer 1 according to an embodiment of the present invention. The spectroscopic ellipsometer 1 is constructed to analyze the optical characteristic of a sample 30 for each layer and to evaluate the electro-optic effect, by generating electric field at the sample 30 having a multilayer film structure and irradiating polarized light. The spectroscopic ellipsometer 1 of the present embodiment comprises a power supply device 18 and a pair of conducting probe stands 19, as voltage applying means for applying voltage for generating electric field at the sample 30.

Figure 3A:
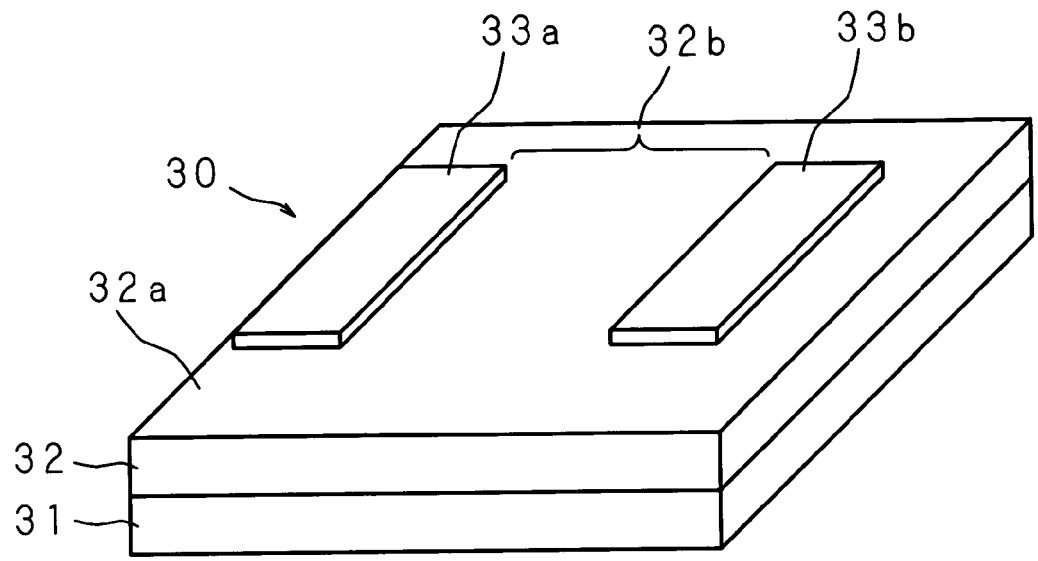
FIG. 3A is a perspective view of a sample.
Figure 4:
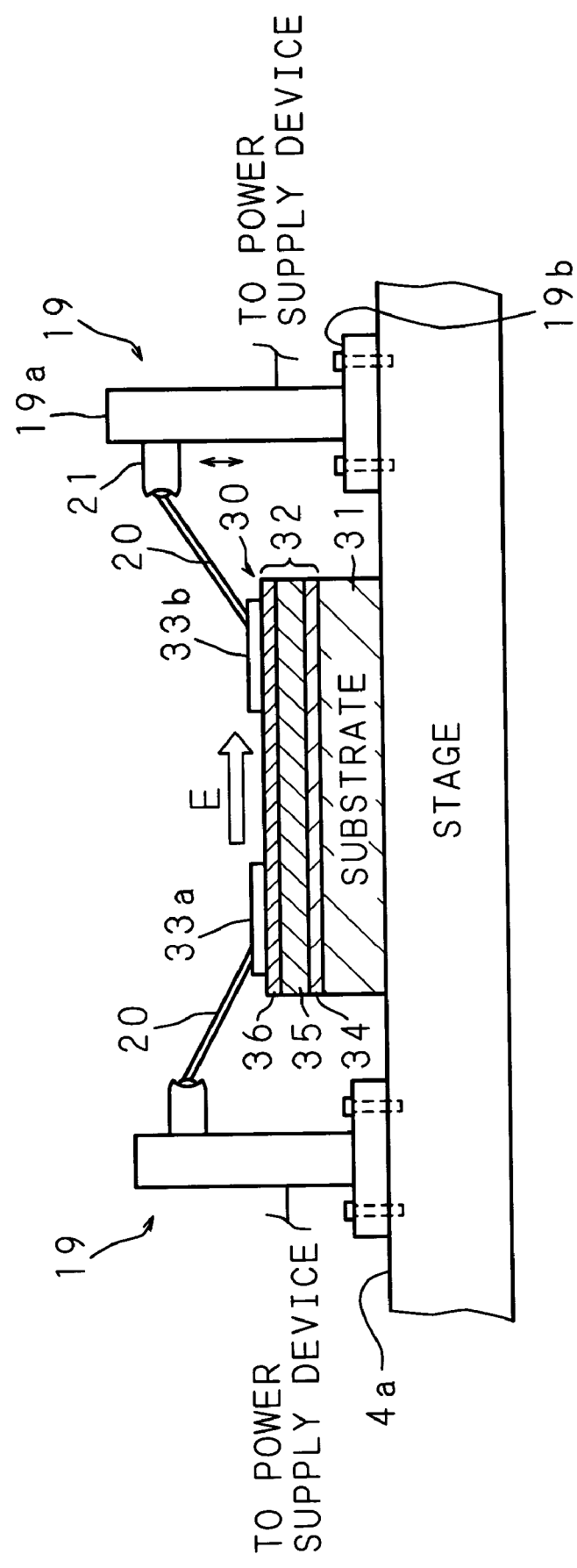
FIG. 4 is a schematic view showing a state of a sample placed on a stage.

Although the spectroscopic ellipsometer 1 can analyze a variety of samples as an object of evaluation, in the present embodiment, as shown in FIGS. 3A and 4, the object of evaluation is the sample 30 constructed by forming a PLZT film 32 on an Si (silicon) substrate 31, which has a Pt (platinum) film provided on the surface thereof by vapor deposition, and providing electrodes 33a and 33b made of $IrO_2$ or W (tungsten) on the film surface of the PLZT film 32. The PLZT film 32 is a ferroelectric film including lead (Pb), lanthanum (La), zircon (Zr) and titanium (Ti) and can be represented as $Pb_{1-X}La_X(Zr_YTi_{1-Y})O_3$ (0<X<0.28, 0<Y<1.0) in detail. Moreover, the PLZT film 32 has a multilayer film structure since an unintended unknown film layer is formed following the formation of the PLZT film 32.

In particular, as shown in FIG. 4, the PLZT film 32 of the sample 30 has a total of three layers: a second film 35 which is a PLZT-based film that is intended to be formed, an unknown first film 34 which is formed following the second film 35 and the film characteristic of which cannot be analyzed with conventional analysis methods, and a third film 36 formed above the second film 35.

Going back to FIG. 2, the structure of the spectroscopic ellipsometer 1 of the present embodiment will be explained. The spectroscopic ellipsometer 1 is divided broadly into a part related to measurement and analysis system, a part related to drive system and a part related to voltage application to the sample 30.

As a part related to measurement and analysis system, the spectroscopic ellipsometer 1 is constructed to connect a xenon lamp 2 and a light polarizer 3 by a first optical-fiber cable 15a, to apply polarized light to the sample 30 placed on a stage 4 (sample support) and to receive light (polarization state of light) reflected from the sample 30 with a light receiver 5. The light receiver 5 is connected with a spectrometer 7 via a second optical-fiber cable 15b, and the spectrometer 7 measures the light for each wavelength and transmits the measurement result to a data acquisition device 8 as an analog signal. The data acquisition device 8 converts the analog signal into a required value and transmits the value to a computer 10, which analyzes it.

Moreover, as a part related to drive system, the spectroscopic ellipsometer 1 has a first motor M1—a sixth motor M6 respectively provided at the stage 4, the light polarizer 3, the light receiver 5 and the spectrometer 7 and controls drive of each motor M1-M6 with a motor controller 9 connected with the computer 10 so that the stage 4, the light polarizer 3, the light receiver 5 and the spectrometer 7 can be suitably moved according to the measurement set up. It should be noted that the motor controller 9 controls drive of each motor M1-M6 on the basis of indication outputted from the computer 10.

Furthermore, as a part related to voltage application, the spectroscopic ellipsometer 1 is provided with the pair of conducting probe stands 19 (corresponding to contact means), which are attached to a stage surface 4a of the stage 4, to come in electrical contact with the sample 30, as described above, and the power supply device 18 (corresponding to power supply means). Voltage is applied to the sample 30 when the power supply device 18 supplies power of a required voltage value to the conducting probe stands 19. The power supply device 18 is connected with the computer 10, and performs initiation and termination of voltage application, setting and modification of a voltage value to be applied and the like on the basis of indication outputted from the computer 10. It should be noted that the spectroscopic ellipsometer 1 has a movable magnifying glass cylindrical portion 17 provided above the sample 30, so that whether the contact state between the conducting probe stands 19 and the sample 30 is appropriate or not can be checked with the magnifying glass cylindrical portion 17.

Next, the respective units 2, 3 and the like described above will be described in detail in order. The xenon lamp 2 is generating means for generating light, which generates white light including a plurality of wavelength components as a light source, and transmits generated white light to the light polarizer 3 via the first optical-fiber cable 15a.

The light polarizer 3 is positioned on a semicircular rail 6, has a polarizer 3a therein, polarizes white light with the polarizer 3a and applies polarized light to the sample 30. Moreover, the light polarizer 3 moves along the rail 6 when the fourth motor M4 is driven, so that an angle (incident angle φ) of irradiated light, with respect to the perpendicular line to the surface of the sample 30, can be adjusted.

The stage 4 is placed on a movable rail portion 4b so as to be slidable and can be moved respectively in the X and Y directions (direction perpendicular to the paper surface of FIG. 2), which cross each other at 90-degrees, and in the Z direction that is a height direction, of a stage surface 4a on which the sample 30 is placed, by driving the first motor M1—third motor M3 (corresponding to moving means). By moving the stage 4, light can strike a variety of locations of the sample 30 and an in-plane analysis of the sample 30 can be made. It should be noted that the stage 4 is provided with a number of screw holes for attaching the pair of conducting probe stands 19, formed on the stage surface 4a, so that each conducting probe stand 19 can be attached to a required location of the stage surface 4a, according to the dimension and the shape of the sample 30.

The light receiver 5 is positioned on the rail 6 similarly to the light polarizer 3, incorporates a PEM (Photo Elastic Modulator) 5a and an analyzer 5b, and guides light reflected from the sample 30 to the analyzer 5b via the PEM 5a. Moreover, the light receiver 5 can be moved along the rail 6 by driving the fifth motor M5 and controlled by the motor controller 9, so that this movement of the light receiver 5 is in conjunction with the movement of the light polarizer 3, and a reflection angle φ and the incident angle φ become the same. It should be noted that the PEM 5a incorporated in the light receiver 5 obtains elliptical polarization from linear polarization, by applying phase-modulation to the received light at a required frequency (50 kHz, for example). Moreover, the analyzer 5b transmits a specified polarization among various polarizations phased-modulated by the PEM 5a.

The spectrometer 7 incorporates a reflecting mirror, a diffraction grating, a photomultiplier (PMT), a control unit and the like, and reflects light transmitted from the light receiver 5 through the second optical-fiber cable 15b with the reflecting mirror, and guides the light to the diffraction grating. The angle of the diffraction grating varies by the sixth motor M6, and the wavelength of the light reflected from the diffraction grating can be changed. The outgoing polarized light is measured by the PMT, and the control unit performs processes of generating an analog signal according to the measured wavelength, and sending the signal to the data acquisition device 8. It should be noted that the photomultiplier may be combined with photodiode arrays (PDA).

The data acquisition device 8 calculates a phase difference Δ and an amplitude ratio Ψ of the polarization state (P polarization, S polarization) of reflected light measured on the basis of the signal from the spectrometer 7, and transmits the calculated result to the computer 10. It should be noted that the phase difference Δ and the amplitude ratio Ψ have the relation represented by the following expression (1) to a complex Fresnel reflection coefficient Rp of P polarized light and a complex Fresnel reflection coefficient Rs of S polarized light.

$$Rp/Rs = \tan\Psi \cdot \exp(i\cdot\Delta) \quad (1)$$

Here, i is an imaginary unit (the same goes for the following). Moreover, Rp/Rs is referred to as a ratio of complex Fresnel reflection coefficient ρ.

Moreover, each conducting probe stand 19 shown in FIG. 4 comprises a square-pole-like stand portion 19a, a plate-like support portion 19b provided at the lower end of the stand portion 19a, a holder portion 21 attached to the stand portion 19a so as to be movable up and down, and a probe 20 to come in contact with the sample 30 and provide conduction. The support portion 19b is provided with through-holes formed on the peripheral corners, and the conducting probe stand 19 is fixed to the stage surface 4a of the stage 4, by inserting a bolt into the through-hole and screwing the bolt in a required screw hole of the stage 4.

Figure 5:
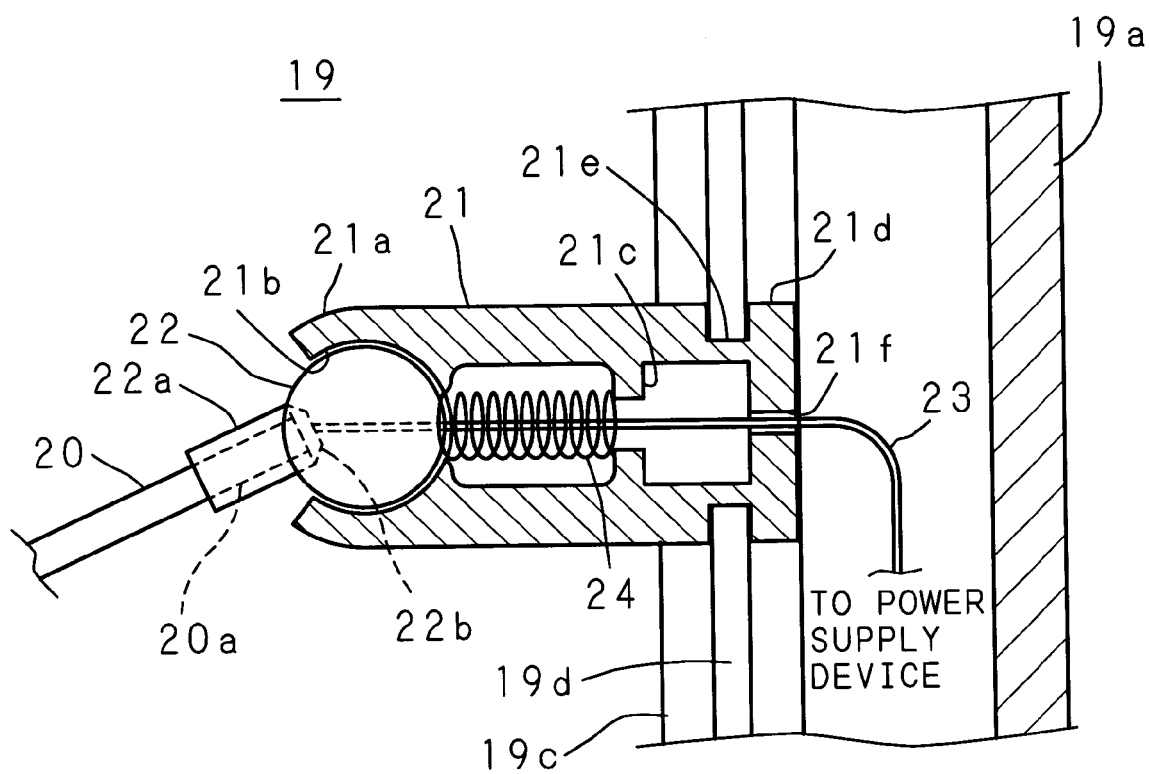
FIG. 5 is a sectional view of a conducting probe stand showing the essential part thereof in an enlarged manner.

As shown in FIG. 5, the stand portion 19a has a cavity therein and is provided with a slit portion 19c, which is formed in the vertical direction and has an aperture having a required width at a side face where the holder portion 21 is attached. A convex rail portion 19d is provided at an end face of this slit portion 19c. Moreover, the holder portion 21 is a short square bar, and an end portion 21d side thereof is engaged with the slit portion 19c of the stand portion 19a, by slight press fitting. In particular, the holder portion 21 is provided with a recess 21e formed at the circumference of the one end portion 21d side, and is constructed to be slidable up and down along the rail portion 19d, with this recess 21e being engaged with the rail portion 19d of the slit portion 19c.

The holder portion 21 also has a cavity therein and is provided with: a spherical depression 21b formed spherically from an end face of the other end portion 21a where the probe 20 is attached; a locking portion 21c projected from a location at a required distance from the spherical depression 21b toward the one end portion 21e; and a through-hole 21f formed at an end face of the one end portion 21e side. The holder portion 21 holds a spherical joint 22 at the spherical depression 21b so as to be rotatable, and a helical compression spring 24 is disposed between the spherical depression 21b and the locking portion 21c so as to press the spherical joint 22 outward.

The spherical joint 22 is provided with: a cylindrical connector portion 22a projected to come in contact with the probe 20; a connecting terminal 22b provided at the internal bottom of the connector portion 22a, to come in electrical contact with the probe 20; and a lead wire 23 extended from this connecting terminal 22b. It should be noted that the lead wire 23 is extended through the cavity inside the holder portion 21 and the through-hole 21f to the cavity inside the stand portion 19a, with a terminal thereof being connected with the power supply device 18.

The probe 20 to be connected with the connector portion 22a of the spherical joint 22 is an acicular conductive material comprising a required rigidity for contact with the sample 30, and an end face of an end portion 20a of the probe 20 comes in contact with the connecting terminal 22b of the spherical joint 22, and provides conduction, when the probe 20 comes in contact with the connector portion 22a. The probe 20 connected with the connector portion 22a can move an end thereof, which is to come in contact with the sample 30, right, left, up and down, by rotating the spherical joint 22. Moreover, since the spherical joint 22 is pressed by the helical compression spring 24, it is possible to maintain the probe 20 in a variety of orientation, and to ensure a contact pressure against the sample 30 appropriate for conduction. It should be noted that a conducting probe stand 19 which lies on the left in FIG. 4 is of positive electrode side, and the other conducting probe stand 19 which lies on the right is of negative electrode side in the present embodiment.

Figure 6:
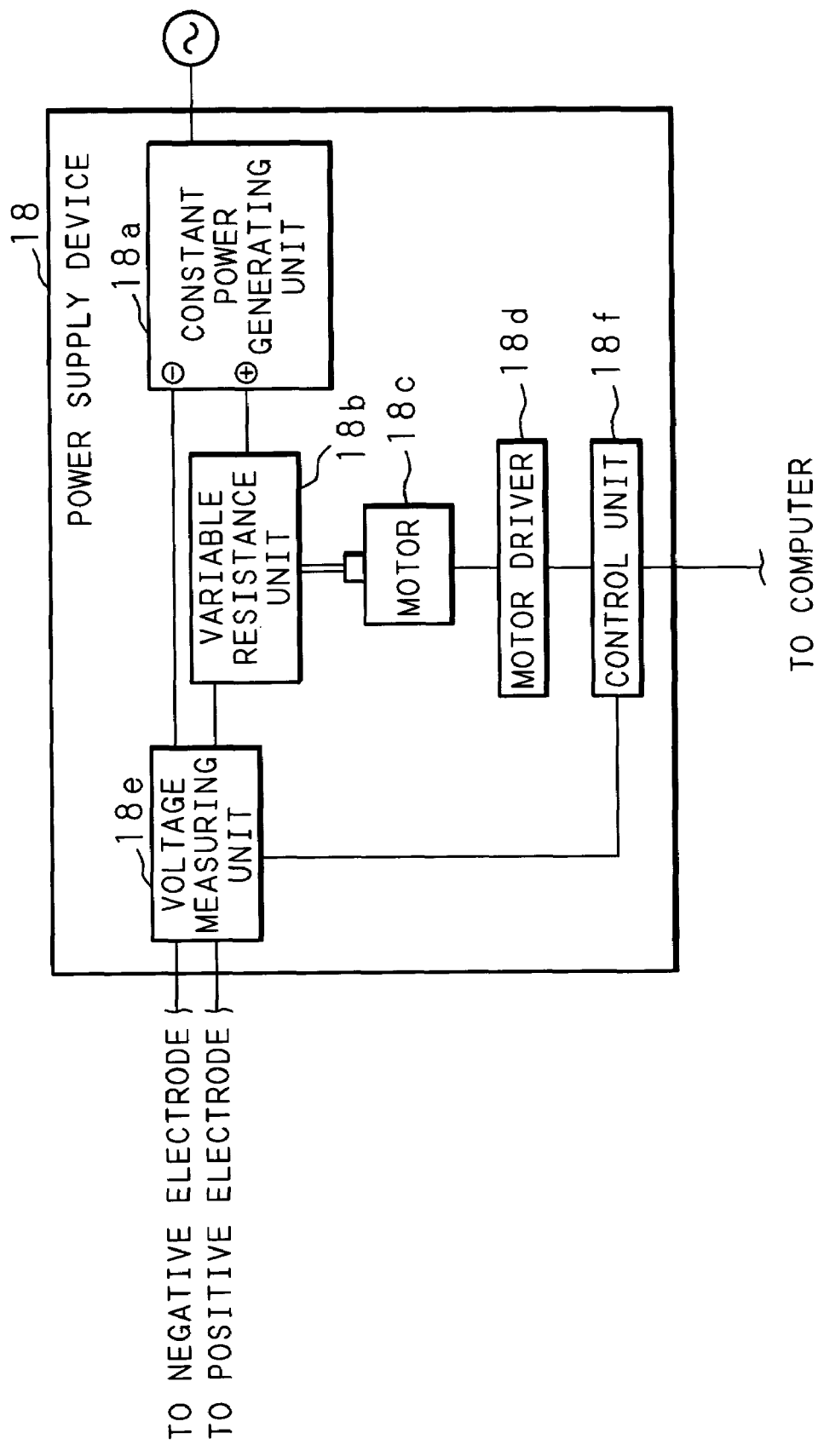
FIG. 6 is a block diagram showing the internal structure of a power supply device.

Moreover, the power supply device 18 shown in FIG. 6 corresponds to power supply means and comprises a constant power generating unit 18a, a variable resistance unit 18b, a motor 18c, a motor driver 18d, a voltage measuring unit 18e and a control unit 18f therein. The constant power generating unit 18a is connected with an alternating-current commercial power source AC and generates direct-current voltage of a required voltage value from alternating-current voltage. The variable resistance unit 18b is connected with + side of the constant power generating unit 18a, and changes the resistance value by drive of the motor 18c. This change in the resistance value of the variable resistance unit 18b causes a change in the voltage value of electric power outputted from the power supply device 18. It should be noted that the motor 18c is operated by a drive amount based on a signal from the motor driver 18d, and the motor driver 18d is controlled by the control unit 18f.

The voltage measuring unit 18e is connected with the variable resistance unit 18b and—side of the constant power generating unit 18a in parallel, measures a voltage value of electric power outputted from the power supply device 18 and sends the measured result to the control unit 18f. The control unit 18f is connected with the computer 10 and controls a voltage value of electric power to be outputted from the power supply device 18, on the basis of an indication signal of the computer 10. In particular, upon receiving an indication signal defining a voltage value from the computer 10, the control unit 18f outputs a signal including indication for driving the motor 18c to the motor driver 18d, so as to achieve the defined voltage value. Moreover, the control unit 18f performs processes of receiving measurement result from the voltage measuring unit 18e, detecting whether a voltage value of electric power to be outputted is different from a voltage value defined by the computer 10 or not, and outputting drive control indication of the motor 18c to the motor driver 18d, so as to correct the voltage value of output to be the defined value when difference is detected.

On the other hand, the computer 10 shown in FIG. 2 analyzes the sample 30, on the basis of the phase difference Δ and the amplitude ratio Ψ of the polarization state obtained by the data acquisition device 8, performs movement of the stage 4 during measurement, and controls the voltage to be applied to the sample 30 and the like.

The computer 10 comprises a computer body 11, a display 12, a keyboard 13, a mouse 14 and the like, and the computer body 11 is provided with a CPU 11a, a storage unit 11b, a RAM 11c, a ROM 11d and an attachment interface 11e which are connected by an internal bus. The CPU 11a performs later-described various processes, according to various computer programs stored in the storage unit 11b. The RAM 11c temporarily stores various data and the like related to processes. The ROM 11d stores the content and the like related to the function of the computer 10. The attachment interface 11e is connected with the data acquisition device 8, the motor controller 9 and the power supply device 18, and transmits and receives signals and various kinds of data.

It should be noted that the storage unit 11b of the computer 10 preliminarily stores a computer program for sample analysis, a computer program for movement control of the stage 4, a computer program for voltage control and the like, and also stores known data related to manufacturing processes of the sample 30, a plurality of dispersion formulas to be utilized for the formation of a model, reference data according to various kinds of samples and the like.

Regarding analysis of the sample 30, the computer 10 analyzes the refractive index and the extinction coefficient of the PLZT film 32 as optical characteristic of the sample 30 and the thickness of the PLZT film 32 for each layer, and makes an analysis of the substrate 31 and the like. In particular, when the complex refractive incidies of the substrate 31 and the ambient of the sample 30 are known from the measured phase difference Δ and the measured amplitude ratio Ψ, the computer 10 obtains the thickness and the complex refractive index of the first film 34—third film 36, by forming a model corresponding to the material structure of the sample 30, using a modeling program previously stored in the storage unit 11b. When n represents the refractive index of the film to be analyzed and k represents the extinction coefficient, the complex refractive index N can be calculated from the following optical expression (2):

$$N = n - ik \quad (2)$$

Moreover, assuming that the wavelength of light to be irradiated by the light polarizer 3 is λ, the phase difference Δ and the amplitude ratio Ψ calculated by the data acquisition device 8 have the relation of the following expression (3) to the thickness d of a film to be analyzed, the refractive index n and the extinction coefficient k.

$$(d, n, k) = F(\rho) = F(\Psi(\lambda, \phi), \Delta(\lambda, \phi)) \quad (3)$$

It should be noted that the computer 10 performs a process (fitting) of changing the thickness, parameters of the dispersion formula and the like, so that a difference between a model spectrum $(\Psi_M(\lambda_i), \Delta_M(\lambda_i))$ obtained theoretically from the formed model and a measured spectrum $(\Psi_E(\lambda_i), \Delta_E(\lambda_i))$ related to the measurement result obtained by the data acquisition device 8 becomes minimal, using the thickness of a film, to be analyzed, and a dispersion formula, which represents the wavelength dependence of the complex dielectric constant and includes a plurality of parameters. It should be noted that an example of the dispersion formula to be applied is represented by the following expression (4).

$$\varepsilon = \varepsilon_\infty + \frac{(\varepsilon_S - \varepsilon_\infty)\varpi_t^2}{\varpi_t^2 - \varpi^2 + i\Gamma_0\varpi} + \frac{\varpi_P^2}{-\varpi^2 + i\Gamma_D\varpi} + \sum_{j=1}^{2} \frac{f_j \varpi_{oj}^2}{\varpi_{oj}^2 - \varpi^2 + i\gamma_j\varpi} \quad (4)$$

In the expression (4), ε at the left-hand side denotes a complex dielectric constant, $\varepsilon_\infty$ and $\varepsilon_S$ denote dielectric constants, $\Gamma_0$, $\Gamma_D$ and $\gamma_j$ denote damping factors, and $\omega_{oj}$, $\omega_t$ and $\omega_P$ denote angular frequencies (oscillator frequency, transverse frequency, plasma frequency). It should be noted that $\varepsilon_\infty$ is a dielectric constant at high frequency (high frequency dielectric constant) and $\varepsilon_S$ is a dielectric constant at low frequency (static dielectric constant). Moreover, the complex dielectric constant ε (corresponding to ε(λ)) and the complex refractive index N (corresponding to N(λ)) have the relation of the following expression (5).

$$\epsilon(\lambda) = N^2(\lambda) \quad (5)$$

To give a simplified explanation of the fitting, assuming that T measurement data pairs in a case of measurement of the sample 30 are Exp (i=1, 2, . . . , T) and data pairs calculated from the model, are Mod (i=1, 2, . . . , T), the mean square error $\chi^2$, on the least squares method, using $\sigma_i$ as the standard deviation, is obtained by the following expression (6) since the measurement error is to be normally distributed. It should be noted that P is the number of parameters. When the value of the mean square error $\chi^2$ is small, the coincidence between the measurement result and the formed model is large, and the minimal value of the mean square error $\chi^2$ obtained by comparing a plurality of models corresponds to the best model.

$$\chi^2 = [1/(2T-P)] \sum_{i=1}^{T} (Exp_i - Mod_i)^2 / \sigma_i^2 \tag{6}$$

A sequence of steps of processes related to sample analysis, to be performed by the computer 10, described above, are defined in a computer program for sample analysis stored in the storage unit 11b, and the steps programmed in this computer program include a process to display a menu for inputting and setting the thickness or the like, as items of conditions of a model to be formed corresponding to physical properties of the sample, on the screen of the display 12, or the like. By performing the analysis process described above, the computer 10 can analyze the PLZT film 32 of the sample 30 for each layer 34-36. It should be noted that the analysis process is programmed so as to be performed for each movement of the stage 4 and for each change of the voltage value to be applied, which will hereinafter be described.

Figure 3B:
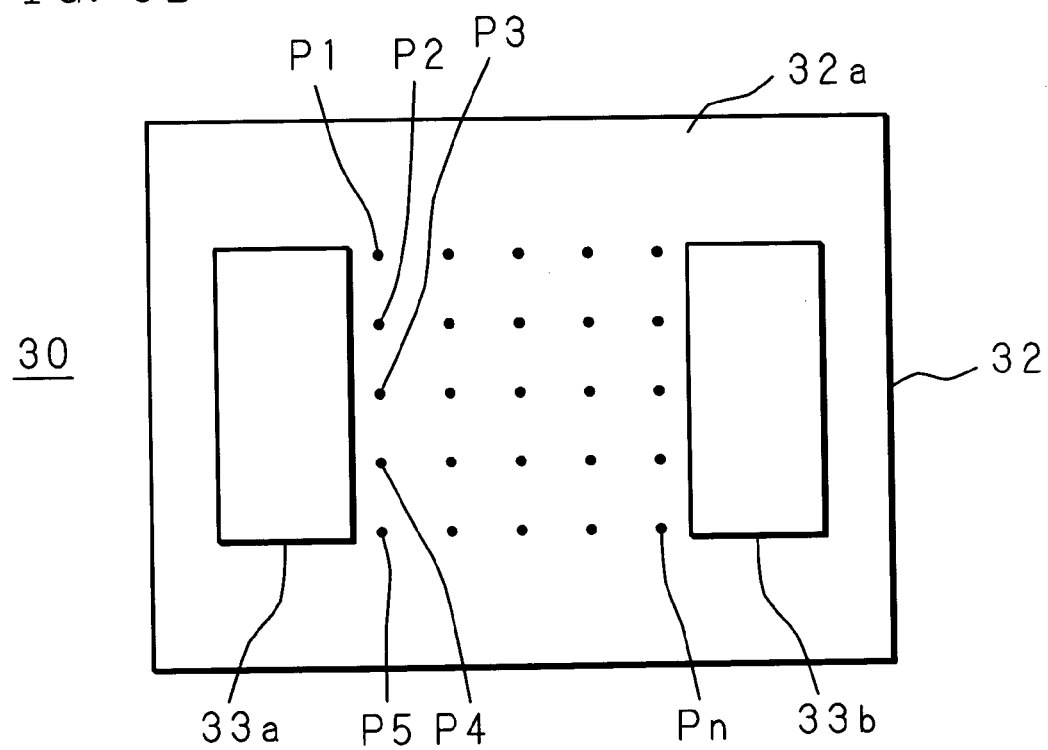
FIG. 3B is a plan view of the sample.

Moreover, regarding the movement of the stage 4 during measurement, the computer 10 performs a process of accepting specification of points (locations) P1-Pn of the sample 30 shown in FIG. 3B to which light is to be irradiated and controlling movement of the stage 4 so that light is sequentially irradiated to the specified points P1-Pn, a process of judging whether the stage 4 was moved to all the specified points or not, and the like, on the basis of the specified content of the computer program for movement control. Regarding the points P1-Pn, the number of points, the positions of the points and the like can be specified in the menu displayed on the screen of the display 12. It should be noted that a portion 32b (see FIG. 3A) of a film surface 32a of the PLZT film 32 between electrodes 33a and 33b of the sample 30 is a specified area of the points P1-Pn in the present embodiment.

Furthermore, regarding control of applied voltage, the computer 10 performs a process of accepting specification of voltage values to be applied to the sample 30 and controlling the power supply device 18 to apply the specified voltage values to the sample 30 before irradiation, and a process of judging whether all the specified voltage values are applied or not, and the like, on the basis of the specified content of the computer program for voltage control. Regarding the respective voltage values to be set, a plurality of voltage values, a method for changing the voltage value and the like can be specified in the menu displayed on the screen of the display 12. It should be noted that, for the sample 30 of the present embodiment, a voltage value of approximately 100-500 V is set as a reference voltage value and settings are made so that the voltage value rises from the reference voltage value to a required number of voltage values at intervals of 5V, for example, and goes back to the reference voltage value.

Next, a sequence of process procedure related to an optical characteristic analysis method for analyzing the sample 30 using the spectroscopic ellipsometer 1 constructed as above will be explained with reference to the flowchart in FIG. 7.

First, the sample 30 is placed on the stage 4 of the spectroscopic ellipsometer 1 (S1). It should be noted that each electrode 33a, 33b of the sample 30 comes in contact with the probe 20 as shown in FIG. 4 when the sample 30 is placed.

Next, the points P1-Pn for measuring the sample 30, the voltage value to be applied, the incident angle $\phi$, conditions (material of the substrate, thickness, optical constant and the like) for model formation according to the sample 30, and the like are inputted into the computer 10 as items related to analysis (S2). It should be noted that the spectroscopic ellipsometer 1 moves the light polarizer 3, the stage 4 and the light receiver 5, so as to give the incident angle $\phi$ and the reflection angle $\phi$ with respect to the first point P1, upon receiving input of the points P1-Pn and the input of the incident angle $\phi$, and the computer 10 forms a model for analysis, upon receiving the input of conditions for the model formation.

Moreover, the spectroscopic ellipsometer 1 applies voltage to the sample 30 from the first voltage value set by input (S3). This voltage application causes generation of electric field E in the direction shown in FIG. 4 between the electrodes 33a and 33b of the sample 30. In this state, the spectroscopic ellipsometer 1 applies polarized light to the sample 30 from the light polarizer 3 (S4) and measures the phase difference $\Delta_E$ and the amplitude ratio $\Psi_E$ (S5).

Moreover, the spectroscopic ellipsometer 1 calculates the phase difference $\Delta_M$ and the amplitude ratio $\Psi_M$ from the model with the computer 10, performs fitting for the thickness of the model, parameters of the dispersion formula and the like so that the difference between the measured values and the calculated values of the model becomes minimal, and, when the difference obtained by the least squares method after the fitting falls in a required value (becomes sufficiently small), analyzes the thickness, the optical constants (refractive index n, extinction coefficient k) and the like of the sample 30 for each layer from values such as thickness and parameters of the dispersion formula at this time (S6).

Next, the spectroscopic ellipsometer 1 judges whether all the points P1-Pn set by input are analyzed or not (S7) and, when any one of the points P1-Pn is not analyzed (S7: NO), moves the stage 4 so that light strikes the next set point (S8) and goes back to the process stage (S4) of applying polarized light. As the following process, the process stages S4-S8 are repeated until analysis of all the points P1-Pn is completed and an analysis is made for each point.

Moreover, when it is judged that analysis of all the points P1-Pn is completed (S7: YES), the spectroscopic ellipsometer 1 judges whether an analysis is made by all the voltage values inputted or not (S9). When it is judged, that analysis at any of the voltage values is not completed (S9: NO), the spectroscopic ellipsometer 1 changes the voltage value according to the set order (S10) and goes back to the process stage (S4) of applying polarized light. As the following process, the process stages S4-S10 are repeated until analysis by all the voltage values is completed and an analysis is made for each voltage value.

Lastly, when it is judged that analysis by all the voltage values is completed (S9: YES), the analysis process by the spectroscopic ellipsometer 1 is terminated. Thus, since the spectroscopic ellipsometer 1 according to the present invention makes a sample analysis for each layer automatically, with voltage being applied, it is possible to obtain the refractive index and, furthermore, light transmittance and the like, to evaluate the electro-optic effect of the sample, having a multilayer film structure, for each layer, and to measure a plurality of points P1-Pn and analyze at each point, thereby making an in-plane analysis of electro-optic effect. Especially, with the sample 30 according to the present embodiment, the characteristic of the respective film layers of the PLZT film 32 can be analyzed individually for each layer and, therefore, the present invention can greatly contribute to the research of the sample 30, transfer of the sample preparation process from the research stage to the manufacturing stage, manufacturing control and the like.

It should be noted that the spectroscopic ellipsometer 1 and the optical characteristic analysis method according to the present invention are not limited to the form described above, and various kinds of modified examples may be applied. For example, although the spectroscopic ellipsometer 1 of the present embodiment is constructed to perform process from voltage application to sample analysis automatically, a spectroscopic ellipsometer may have a structure with which one of or both operations of voltage application and movement of the stage 4 are performed manually. When voltage application is performed manually, the process related to voltage control by the computer 10 and the configuration related to voltage value change of the power supply device 18 through the motor 18c and the like can be suitably omitted, while, when movement of the stage 4 is performed manually, the process related to movement of the stage 4 of the computer 10 and the first motor M1-third motor M3 can be omitted. Is should be noted that the conducting probe stands 19 should be provided at locations which do not obstruct irradiation and reflection of light, when the stage 4 is not moved.

Figure 7:
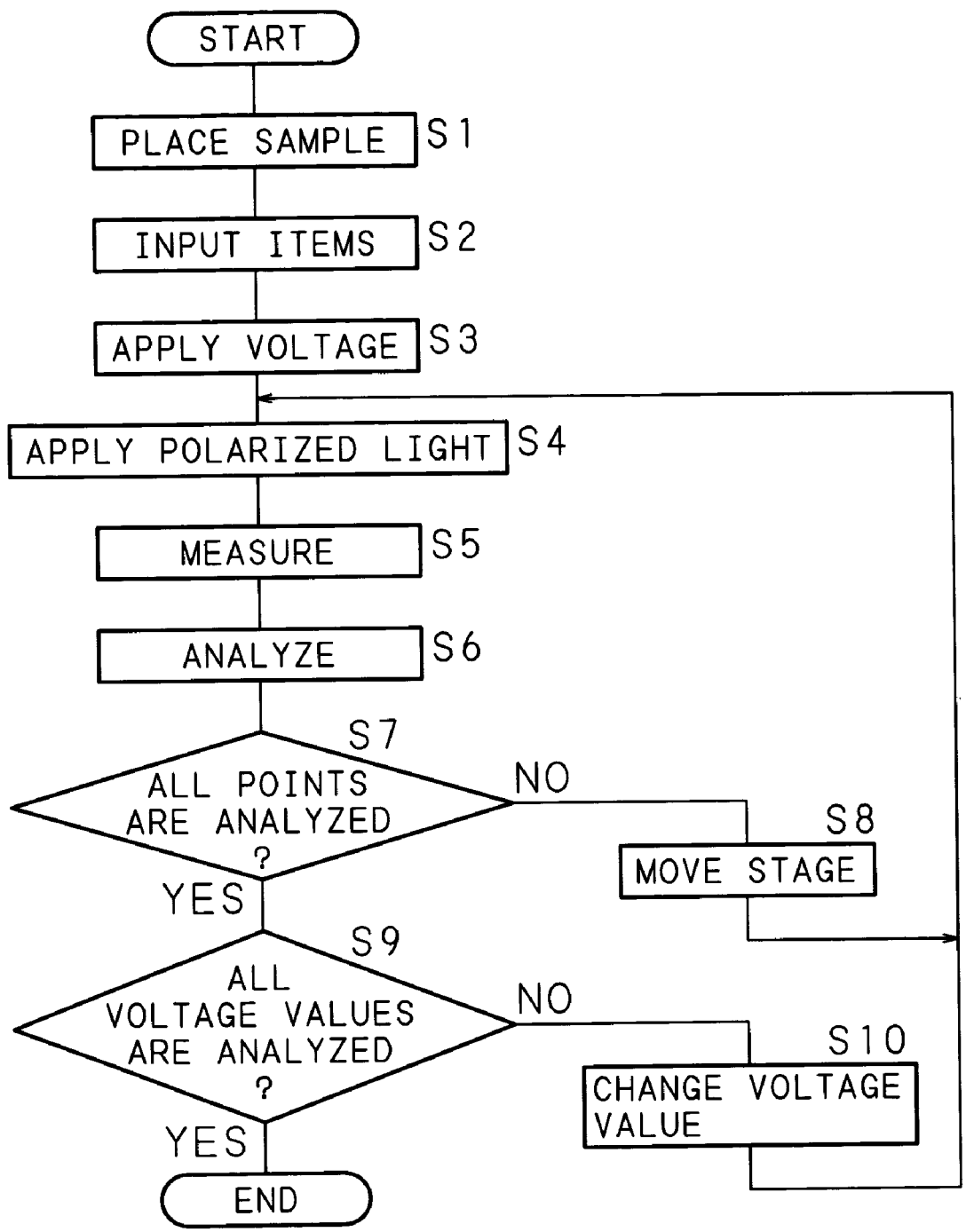
FIG. 7 is a flowchart showing the process procedure related to an optical characteristic analysis method.

Moreover, when it is needless to analyze a plurality of points of a sample, the process shown by S7 and S8 in the flowchart according to the optical characteristic analysis method shown in FIG. 7 can be omitted, while, when it is needless to analyze by changing the voltage value, the process shown by S9 and S10 in the flowchart according to the optical characteristic analysis method can be omitted.

Figure 8:
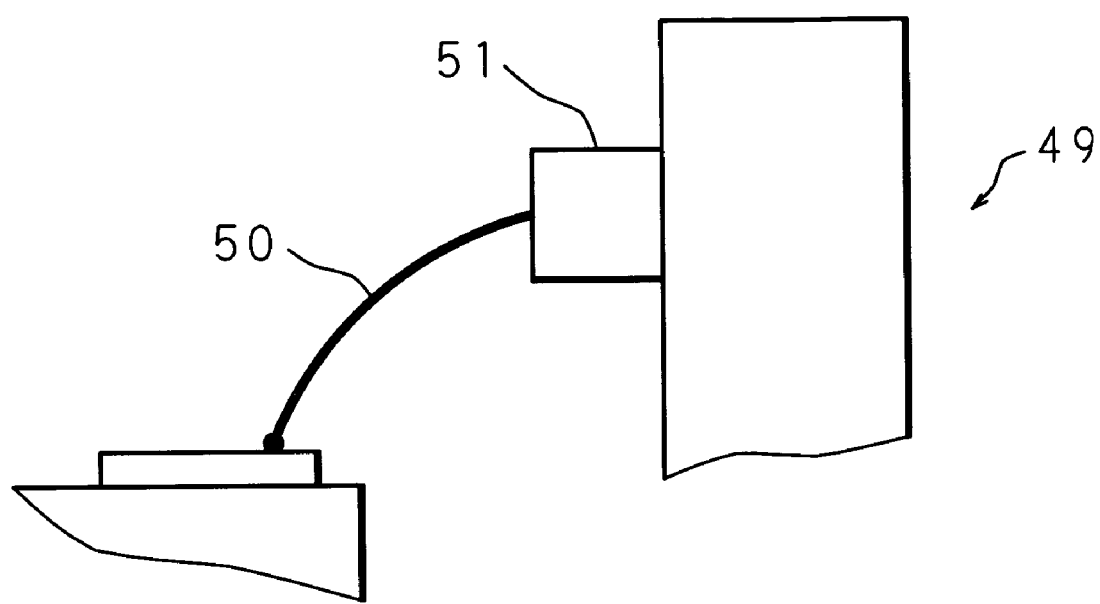
FIG. 8 is a schematic view showing a conducting probe stand of a modified example.

Furthermore, instead of applying the conducting probe stands 19 and the probes 20 shown in FIGS. 4 and 5 for contact with the sample, the spectroscopic ellipsometer 1 may be provided, for example, with a bonding wire 50 extended from a holder 51 provided at a conducting probe stand 49 as shown in FIG. 8, thereby providing conduction with the sample by the bonding wire 50.

Furthermore, the analysis object of the spectroscopic ellipsometer 1 is not limited to a sample having a PLZT film, and the spectroscopic ellipsometer can suitably analyze a sample having a PZT film of a ferroelectric film obtained by mixing lead titanate ($PbTiO_3$) and lead zirconate ($PbZrO_3$), a sample having a high-dielectric constant multilayer film structure, a sample having a ferroelectric multilayer film structure and the like, and, moreover, can also analyze various kinds of samples having a film formed on a substrate.

Figure 9:
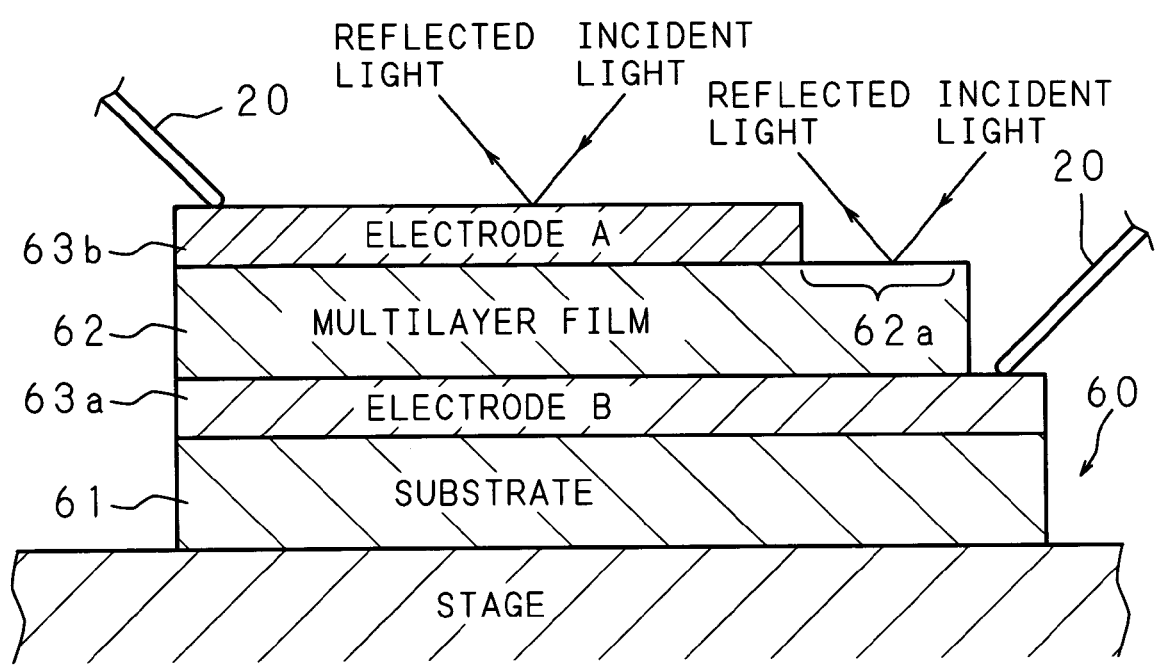
FIG. 9 is a schematic view showing a sample having a structure, which is to be analyzed with the present invention.

Moreover, the structure of a sample which can be analyzed by the spectroscopic ellipsometer 1 is also not limited to the form shown in FIGS. 3A, 3B and 4, and a sample 60 having a structure shown in FIG. 9 can also be analyzed. To explain the structure of the sample 60 with reference to FIG. 9, the sample 60 is provided with a multilayer film 62 formed on the substrate 61 so as to be sandwiched between an electrode B 63a and an electrode A 63b. Since the area of the multilayer film 62 in the plane direction is slightly smaller than the electrode B 63a, the surface of a right end portion of the electrode B 63a is exposed and a surface portion 62a (right end) of the multilayer film 62 is not covered with the electrode A 63b. It should be noted that the spectroscopic ellipsometer 1 can analyze the multilayer film for each layer, when the multilayer film 62 is a high-dielectric constant film or a ferroelectric film having a dielectric constant larger than or equal to 50 based on electric measurement.

When the sample 60 having the structure described above is analyzed, one of the pair of probes 20 comes in contact with the electrode A 63b as shown in FIG. 9 and the other comes in contact with an exposed surface portion of the electrode B 63a, and voltage is applied in this state. It should be noted that, when the multilayer film 62 has, for example, a three-layer structure, a voltage value V1 is applied to the upper layer, a voltage value V2 is applied to the middle layer and a voltage value V3 is applied to the lower layer, and an applied voltage value represented by V has the relation of: V1+V2+V3=V. Moreover, in this case, the direction of the electric field to be generated by voltage application is a direction which connects the electrode A 63b and the electrode B 63a so as to cross the multilayer film 62 vertically. Since the electric field is applied in a direction across the multilayer film 62 and the electro-optic effect tends more to occur, it is possible to set the applied voltage to lower values in comparison with the sample 32, as shown in FIG. 3A, for example, the reference voltage values could be set approximately 1-10 V.

Moreover, the area of the sample 60, shown in FIG. 9, to which light strikes, is the exposed surface portion 62a of the multilayer film 62. Furthermore, when the electrode A 63b, covering the multilayer film 62, is a transparent electrode having optical transparency, or when the electrode A 63b is thin enough to transmit light, it also becomes possible to measure from above the electrode A 63b, i.e. by applying light to the surface of the electrode A 63b. It should be noted that, when light strikes from above the electrode A 63b, the electrode A 63b also influence measurement and analysis and, therefore, it is necessary to input the material, the thickness and the like of the electrode A 63b in the stage (S2) of inputting items of the flowchart shown in FIG. 7.

Furthermore, the present invention does not always have to be constructed based on a spectroscopic ellipsometer, and may be embodied as a structure obtained by combining a measuring and analyzing apparatus, which comprises generating means for generating light having a plurality of wavelength components such as the xenon lamp 2, irradiating means for polarizing generated light and irradiating the light to a sample placed on a sample support such as the light polarizer 3 and measuring means for detecting and measuring light reflected from the sample such as the light receiver 5 and the spectrometer 7, with voltage applying means such as the power supply device 18 and the conducting probe stands 19. In this structure, the irradiating means irradiates polarized light to a sample, with voltage being applied thereto, by the voltage applying means, and the measuring means measures.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. An optical characteristic analysis method for analyzing optical characteristic of a sample comprising a film of a plurality of layers with a spectroscopic ellipsometer, comprising the steps of:
applying a voltage to the sample;
irradiating polarized light, having a plurality of wavelength components, to a film surface of the sample to which the voltage is applied;
measuring a polarization state of light reflected from the sample for each of at least more than one of the plurality of wavelength components; and
generating data representing an optical characteristic of the film by analyzing each of at least more than one of the plurality of layers, based on the measured polarization state of light for each of the at least more than one wavelength components.

2. The optical characteristic analysis method according to claim 1, wherein a value of the voltage to be applied is changed, and the irradiating step and the measuring step are performed for each value of the changed voltage.

3. The optical characteristic analysis method according to claim 2, wherein a location where light is irradiated is sequentially moved in the irradiating step and optical characteristic is analyzed for each moved location in the measuring step.

4. The optical characteristic analysis method according to claim 1, wherein a location where light is irradiated is sequentially moved in the irradiating step and the optical characteristic is analyzed for each moved location in the measuring step.

5. The optical characteristic analysis method according to claim 1, wherein the analyzing step further comprises the steps of:
forming an optical model corresponding to a material structure of the plurality of layers of the sample, and
fitting the model to the measured polarization state of light for each of the at least more than one of the plurality of wavelength components.

6. An optical characteristic analysis method for analyzing optical characteristic of a sample, which comprises a film of a plurality of layers and a plurality of electrodes and has an optically transparent electrode covering the film among the plurality of electrodes, with a spectroscopic ellipsometer, comprising the steps of:
applying a voltage across the electrodes of the sample:
irradiating polarized light having a plurality of wavelength components to a surface of the optically transparent electrode of the sample to which the voltage is applied;
measuring a polarization state of light reflected from the sample for each of at least more than one of the plurality of wavelength components; and
generating data representing an optical characteristic of the film by analyzing each of at least more than one of the plurality of layers, based on the measured polarization state of light for each of the plurality of wavelength components.

7. The optical characteristic analysis method according to claim 6, wherein a value of voltage to be applied is changed, and the irradiating step and the measuring step are performed for each value of changed voltage.

8. The optical characteristic analysis method according to claim 7, wherein a location where light is irradiated is sequentially moved in the irradiating step and optical characteristic is analyzed for each moved location in the measuring step.

9. The optical characteristic analysis method according to claim 6, wherein a location where light is irradiated is sequentially moved in the irradiating step and optical characteristic is analyzed for each moved location in the measuring step.

10. A sample measuring apparatus for measuring a sample comprising a film having a plurality of layers, the sample measuring apparatus comprising:
a generating unit for generating light having a plurality of wavelength components;
an irradiating unit for polarizing the light generated by the generating unit, and irradiating the polarized light having a plurality of wavelength components to a sample placed on a sample support;
a measuring unit for detecting and measuring each of at least more than one the plurality of wavelength components of the polarized light that are reflected from the sample; and
a voltage applying unit for applying voltage to the sample placed on the sample support,
wherein:
the irradiating unit is constructed to irradiate light to the sample to which the voltage applying unit applies voltage,
the voltage applying unit is attached to the sample support and comprises a contact unit for coming into contact with the sample, and
the sample measuring apparatus is adapted to generate data representing an optical characteristic of the film by analyzing each of at least more than one of the plurality of layers, based on a measured polarization state of light for each of at least more than one of the plurality of wavelength components.

11. A spectroscopic ellipsometer for irradiating polarized light to a sample comprising a film having a plurality of layers and that has been placed on a sample support, and for analyzing a characteristic of the sample on the basis of a measurement of a polarization state of light reflected from the sample, comprising:
a voltage applying unit for applying voltage to the sample placed on the sample support, wherein:
an analysis is made by irradiating polarized light having a plurality of wavelength components to the sample to which the voltage applying unit applies voltage,
the voltage applying unit is attached to the sample support and comprises a contact unit for coming into contact with the sample, and
the spectroscopic ellipsometer is adapted to generate data representing an optical characteristic of the film by analyzing each of at least more than one of the plurality of layers, based on a measured polarization state of light for each of at least more than one of the plurality of wavelength components.

12. The spectroscopic ellipsometer according to claim 11, wherein the voltage applying unit further comprises a power supply unit for supplying power to the contact unit, and the power supply unit is constructed so as to change a voltage value of the power supply.

13. The spectroscopic ellipsometer according to claim 12, further comprising a controller, capable of performing an operation of analyzing the sample for each voltage value changed by the power supply unit.

14. The spectroscopic ellipsometer according to claim 13, further comprising a moving unit for moving the sample support, wherein the contact unit is provided at the sample support.

15. The spectroscopic ellipsometer according to claim 14, wherein the analyzing unit is operable to analyze the sample for each movement made by the moving unit.

16. The spectroscopic ellipsometer according to claim 12, further comprising a moving unit for moving the sample support, wherein the contact unit is provided at the sample support.

17. The spectroscopic ellipsometer according to claim 16, wherein the analyzing unit is operable to analyze the sample for each movement made by the moving unit.

* * * * *